(12) United States Patent \
Bauer

(10) Patent No.: US 9,199,018 B2 \
(45) Date of Patent: Dec. 1, 2015

(54) SYSTEM AND METHOD FOR MANAGING A SUPPLY OF BREAST MILK

(71) Applicant: MEDELA HOLDING AG, Baar (CH)

(72) Inventor: Ryan Bauer, Fox River Grove, IL (US)

(73) Assignee: MEDELA HOLDING AG, Baar (CH)

( * ) Notice: Subject to any disclaimer, the term of this patent is extended or adjusted under 35 U.S.C. 154(b) by 0 days.

(21) Appl. No.: 14/208,054

(22) Filed: Mar. 13, 2014

(65) Prior Publication Data

US 2014/0263611 A1 Sep. 18, 2014

Related U.S. Application Data

(60) Provisional application No. 61/780,029, filed on Mar. 13, 2013.

(51) Int. Cl.
*G06F 17/00* (2006.01)
*A61M 1/06* (2006.01)
*A61B 19/00* (2006.01)

(52) U.S. Cl.
CPC .................. *A61M 1/06* (2013.01); *A61B 19/44* (2013.01); *A61B 2019/442* (2013.01)

(58) Field of Classification Search
CPC ..... G06Q 30/02; G06Q 10/087; G06Q 10/08; G06Q 7/1008
USPC .................................................. 235/375, 385
IPC ........ G06Q 30/02, 10/087, 10/08; G07F 7/1008
See application file for complete search history.

(56) References Cited

U.S. PATENT DOCUMENTS

| 8,172,129 | B1 | 5/2012 | Laurenzi et al. |
| 2006/0178578 | A1 | 8/2006 | Tribble et al. |
| 2008/0177224 | A1 | 7/2008 | Kelly et al. |
| 2008/0217391 | A1 | 9/2008 | Roof et al. |
| 2009/0157428 | A1 | 6/2009 | Auchinleck |
| 2010/0318377 | A1 | 12/2010 | Lair |
| 2011/0004154 | A1 | 1/2011 | Van Schijndel et al. |

OTHER PUBLICATIONS

Ensmiger, T., et al., "Reading Barcodes Etched on Shiny Surfaces Using Basic Image Processing," 6 pages [online], [retrieved on Aug. 29, 2014]. Retrieved from the Internet <https://web.archive.org/web/20080701000000*/http://www.ces.clemson.edu/-stb/ece847/fall2004/projects/proj 12.doc>.
International Search Report and Written Opinion for Int. App. No. PCT/US2014/025745, completed Aug. 26, 2014.

*Primary Examiner* — Karl D Frech \
(74) *Attorney, Agent, or Firm* — McDonnell Boehnen Hulbert & Berghoff LLP

(57) ABSTRACT

A system is disclosed for managing a supply of breast milk. In one form the system includes a codified container for receiving expressed breast milk. A computing device receives an image of the expressed milk in the codified container. The codification allows for software to recognize the size and type of the container, as well as scale and orientation, to translate the image into an accurate volume. The milk data is then processed and analyzed to produce feedback regarding the pumping session, such as logs, charts, or reminders. In other embodiments, nipple positioning may be analyzed as well.

51 Claims, 4 Drawing Sheets

SYSTEM AND METHOD FOR MANAGING A SUPPLY OF BREAST MILK

CROSS REFERENCE TO RELATED APPLICATIONS

The present application is a non-provisional of U.S. Application Ser. No. 61/780,029 filed on Mar. 13, 2013, the contents of which are fully incorporated by reference herein.

FIELD OF THE INVENTION

This application relates to a system and method for monitoring, organizing, recording, and troubleshooting the collection and/or dispensing of breast milk.

BACKGROUND

Human breast milk collection, when not fed directly to an infant, is generally expressed into a collection container, such as a bottle or bag. The expression and collection of the breast milk is usually accomplished with the aid of a breastpump. Breast milk is important to the nutritional needs of an infant and requires significant effort on the part of the mother to collect, store, protect, and ultimately feed the milk to the infant.

Mothers have a desire to monitor their milk production to understand how they are performing. Monitoring milk production helps mothers gauge how much milk they have, how effectively they are collecting and expressing milk, and may provide clinical data to a physician for troubleshooting. This type of information is most often manually recorded in a pumping log, which may be in the form of a journal or electronic software in which a mother may enter information regarding her pumping session, including how much milk was collected, the date/time of the collection, which breast(s) the milk was collected from, etc. A manual pumping log is a tedious process as it requires the mother to keep track of her pumping session and write down information. To effectively analyze her performance from the log, the mother would need to enter this data into a computer to evaluate trends and anomalies.

It is desirable, therefore, to provide a system to the mother that can easily and accurately capture and manage milk collection information, that minimizes the effort involved, and that works seamlessly with her lifestyle. With the advances in portable computing power, as demonstrated in the increasing capabilities of smart phones, data can be collected and utilized in situ. A milk collection device that enables automatic data collection through interaction with a computer, such as a smart phone, would be beneficial to mothers.

SUMMARY

A system and method for managing a supply of breast milk is provided. The system includes a codified container for receiving expressed breast milk and a computing device for receiving an image of the expressed milk in the codified container. The codification allows for software to recognize the size and type of the container, as well as to scale and orient, to translate the image into an accurate volume. The milk data is then processed and analyzed to produce feedback regarding the pumping session, such as logs, charts, or reminders.

In one embodiment, a method for managing a supply of breast milk of a mother is disclosed. The method includes receiving, via a computing device, at least one image of a container for receiving expressed breast milk, the container including a codification element associated therewith, recognizing the codification element using the computing device, analyzing the codification element using the computing device, and producing feedback regarding the supply of expressed breast milk based on the analysis.

In yet another embodiment, a non-transitory computer readable medium is disclosed. The computer readable medium has stored thereon instructions executable by a computing device to cause the computing device to perform functions comprising recognizing a codification element associated with a container of expressed breast milk, obtaining information regarding the codification element, analyzing the codification element, and providing information regarding the supply of expressed breast milk based on the analysis.

In yet another embodiment, a container for collecting expressed breast milk from a mother is disclosed. The container includes at least one codification element. The codification element is configured to be analyzed by a computing device to provide analysis and feedback regarding the mother's breast milk supply expressed breast milk within the container.

In yet another embodiment, a method for managing the fit of a mother's nipple within a breastshield is disclosed. The method includes receiving, via a computing device, at least one image of a breastpump kit or portion thereof for receiving expressed breast milk, the breastpump kit including a codification element associated therewith, recognizing the codification element using the computing device, analyzing the codification element using the computing device, and producing feedback regarding the fit of the mother's nipple based on the analysis.

In yet another embodiment, a non-transitory computer readable medium is disclosed. The computer readable medium has stored thereon instructions executable by a computing device to cause the computing device to perform functions comprising recognizing a codification element associated with a breatpumping kit, obtaining information regarding the codification element, analyzing the codification element, and providing information regarding the fit of the mother's nipple within a breastshield based on the analysis.

In yet another embodiment, a collection system for collecting expressed breast milk from a mother is provided. The collection system includes a breastpumping kit including a breast shield, a valve, a connector piece, a collection container, and a breastpump, and at least one codification element. The at least one codification element is configured to be analyzed by a computing device to provide analysis and feedback regarding the fit of the mother's nipple within the breast shield.

These and other features and advantages of the present application will be further understood and appreciated when considered in relation to the following detailed description, taken in conjunction with the drawings, in which:

DETAILED DESCRIPTION

The system of the present application uses a milk collection device that enables breastpumping data collection through interaction with a computing device. The computing device may be a smart phone, a tablet, digital camera, or any other computing device, for example. Many computing devices include a camera capable of taking both pictures and videos. The camera, in combination with a custom software application, may be configured to recognize a codified collection container to determine milk volumes. In one example, the mother pumps breast milk into a codified collection container. The mother then uses her computing device to scan or capture an image of the collection container containing the pumped breast milk. In another embodiment, a video (or series of images) of the collection container may be taken. The collection container codification allows for software to recognize the size and/or type of container, as well as the scale and orientation, in order to appropriately translate the visual image(s) into an accurate volume through a combination of milk level and container type information.

The computing device, using an appropriate software application ("app"), then pulls relevant data from the image or scan to determine milk volume collected, and uses the data to develop a pumping log, performance charts, and/or reminders. The video may be used for real-time performance feedback and/or troubleshooting.

The present system is not only useful to monitor and analyze milk collection, but may also be applied for milk dispensation. Tying the milk data to an inventory management system allows the mother and other vested parties, such as caregivers or healthcare workers, to see her entire supply inventory and status. The system may also detect or create serialization of the collection container if desired, which would enable time-based inventory management such as FIFO (first in, first out) or LIFO (last in, first out). In healthcare settings, serialization is also commonly utilized to manage patient safety such that an infant can be guaranteed to receive his/her mother's own milk.

In addition, the system may be used with real-time performance feedback through video monitoring of the collection, which may yield additional information such as milk ejections and pumping duration, for example. Other example feedback may include flow rate, detection of vacuum settings or changes and cycles through the behavior of the nipple, breast or kit, color shifts in the milk, nipple positioning, etc.

In another embodiment, the system may communicate with or be included within a breastpump. The system may also inform the breastpump of the feedback as part of a closed loop control system, and the breastpump may make adjustments based on the feedback received.

Figure 1:
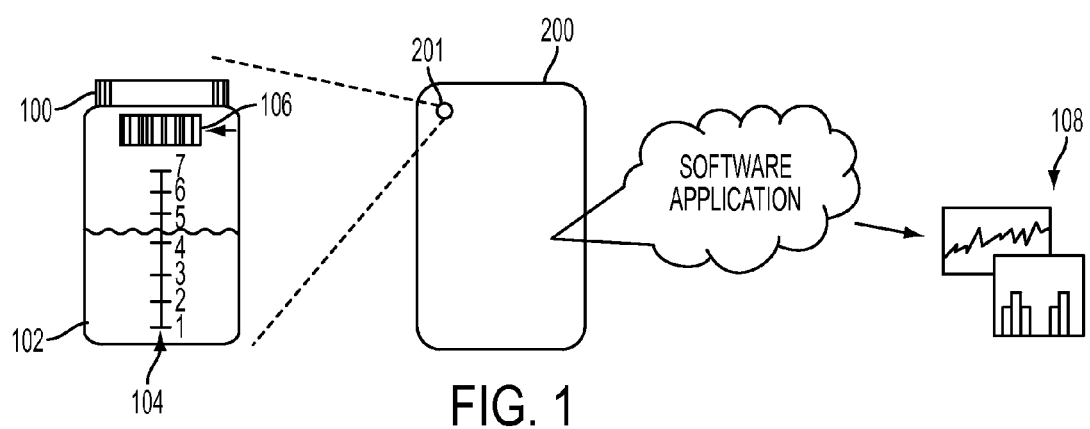
FIG. 1 is a perspective view of an example system according to an embodiment.

FIG. 1 is a perspective view of an example system according to an embodiment. This type of system arrangement is simply illustrative, and not intended to be limiting. Referring to FIG. 1, breast milk 102 is expressed into a container 100 by means of a breastpump, for example. Although the container 100 is shown as a bottle, it should be understood that any suitable container for holding or storing breast milk may be used, such as a bag, for example. The container 100 may include volume markings 104. In one embodiment, the container 100 may further include a codification element 106. Examples of codification elements for the container 100 may include a bar code, a symbol for software container recognition, or any other suitable codification element. The size of the codification element 106 itself may be constrained to provide a reference for the milk level measurement, in the same way that a penny or ruler next to an object in a photograph relates a sense of scale. In other embodiments, the codification element is located within a scanned or captured image of the expressed breast milk, but not on the container. Thus, other items of the collection system within the frame of the image could also contain codification elements to provide image interpretation information for the computing device. Software, such as an application, may process and analyze the data ascribed by the codification element 106 to provide information or feedback 108, such as a pumping log, performance charts, reminders, etc., regarding the mother's breast milk supply.

Other variations of the codification element 106 may include a reading of the volume markings 104 themselves, or the use of a specialized program to analyze one or more features of the container, such as shape, form, or markings of the container to develop a sense of scale. These forms of codification are more discrete, and therefore may provide a more aesthetically pleasing design, while retaining the ability to convey scale and milk level information to the software application. Additional information may be available through the codification element 106, such as a serial number or other manufacturer or marketing data. The codification and milk level data may also be inherently invisible to the human eye, yet detectable through an image with an appropriate detector. For example, thermal signatures, infrared, or ultraviolet could be utilized to detect the codification element 106. The data provided by the codification element(s) of the container may provide identification, scaling, and orientation references (i.e. parameters), or may contain algorithms for the computing device to computationally assess the image. In this sense, the codification element becomes a part of the software and enables execution of the computing device's application.

In another embodiment, multiple codification elements 106 can be present on the container 100. For example, both a separate serial number and a scale element may be utilized. Other codification elements may aid the application in determining the viewing angle for more accurate readings. For example, a circular element will appear more elliptical the more the viewing angle changes from normal to the surface of codification. For video applications, this aids in providing a real time adjustment for container and camera motions. Multiple codifications may also aid in developing a three-dimensional construct of the collection container, which may be used for flexible or shape changing collection containers, such as breast milk collection bags.

After the milk is collected in the codified container 100, a user then scans or takes a picture or video of the container 100 with a computing device 200 having a camera 201. The computing device 200 may comprise a smart phone, tablet, digital camera, or any other type of computing device with the ability to receive an image or video. The computing device 200 is described in detail below with respect to FIG. 5.

Figure 2:
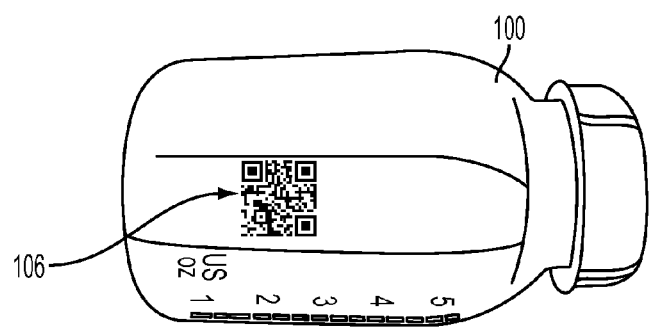
FIG. 2 is a perspective view of an example of a codified container for use with the system shown in FIG. 1.

In one embodiment, advanced image processing can determine milk volumes regardless of container orientation. FIG. 2 is a perspective view of an example of a codified container for use with the system shown in FIG. 1. In the example shown in FIG. 2, a container lies on its side and can be processed by the application through an advanced algorithm enabled by the codification and milk level. This can be useful to obtain data for situations where volumes may not line up with container markings, such as when containers are frozen where milk was not oriented with the graduated markings when placed in the freezer. Additionally, the algorithm may automatically correct for volumetric expansion that occurs when milk is frozen.

In another example embodiment, the codified container may lie upside down. Furthermore, in other embodiments, the computing device may employ its own orientation sensors (such as accelerometers) which can be used for enhancing orientation accuracy and error checking when processing image data.

Further application of the image processing may also yield information regarding features of the milk such as the quality of the milk. For example, the color of the milk can relate to fat content or the inclusion of blood. A history of images of the container 100 could be monitored for any changes to quality of the milk. Additionally, milk that is allowed to sit for a sufficient duration or spun centrifugally will separate into skim and cream. These layers can be detected in the image and volumetrically established to provide nutritional and breast expression information, such as caloric content and degree of breast emptying.

Once the image or video is processed and analyzed by the software application, feedback 108 is given to the user or other interested party in the form of a pumping log, performance charts, reminders, etc. In one example, the feedback is displayed to the user on the computing device 200. In another embodiment, the feedback may be communicated to a healthcare provider at an office or hospital. Other possibilities exist as well.

Figure 3:
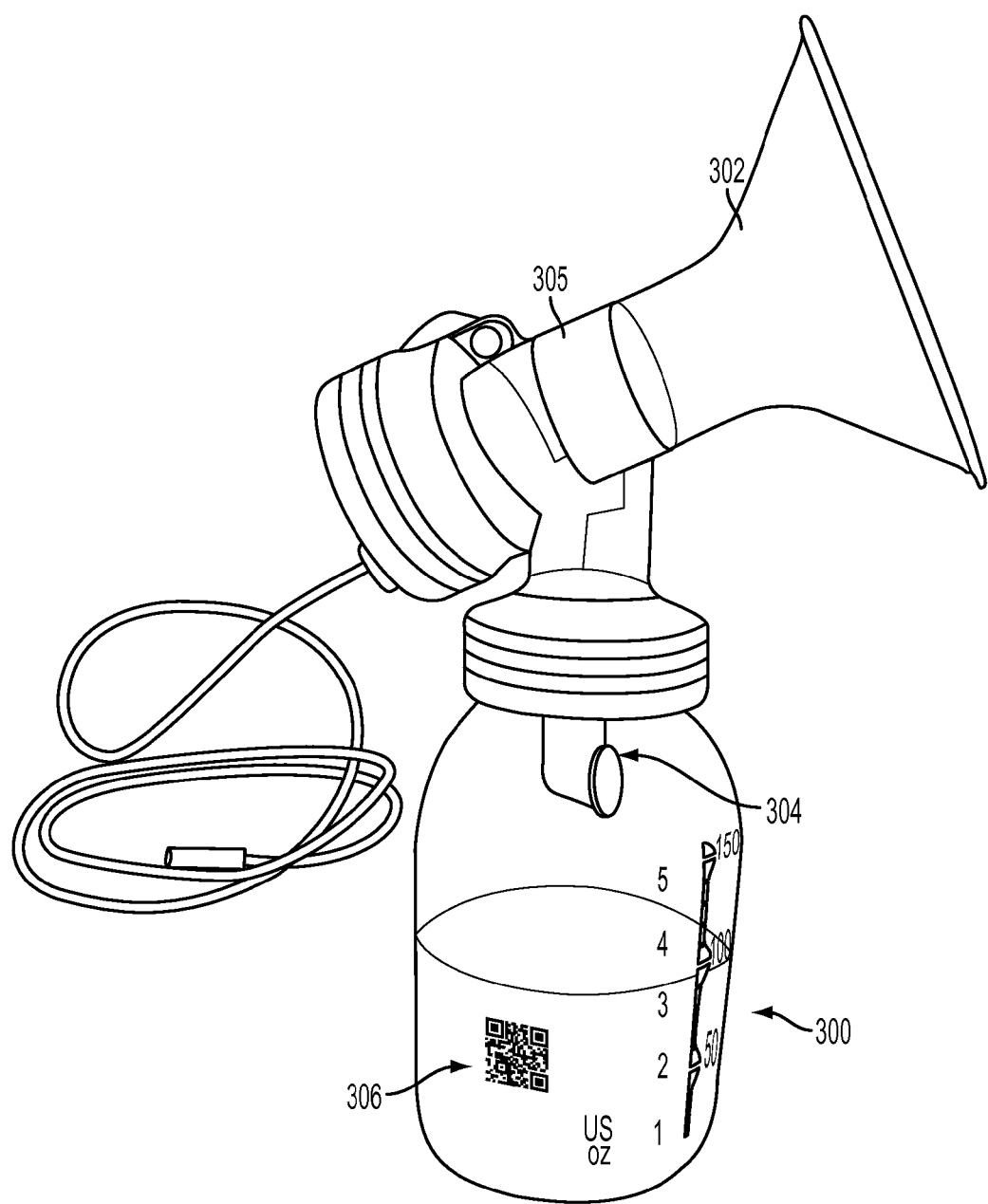
FIG. 3 is a perspective view of an example breastpump kit having a codified container for use with the system shown in FIG. 1.

Referring now to FIG. 3, a collection container 300 for the milk is usually part of a larger assembly of components that comprise a breastpump kit. The kit typically includes a breastshield (funnel) 302, a valve 304, a connector piece 305, and the container 300. The container 300 may include one or more codification elements 306. The codification element 306 may be the same or similar to the codification element 106 described above. Data regarding the pumping session and milk can be collected and analyzed as described above. The image analysis could be further extended to evaluate other aspects of the breastpump kit and the mother. For example, the application may determine if the breastpump kit is configured and attached correctly and provide feedback to the mother. The application may also identify other components employed in the kit and their performance. For example, the breastshield 302 may be provided in different sizes. These sizes could be detected by the application and evaluated in relation to the position of the mother's nipple within the funnel to determine optimal fit and provide recommendations for a different size to the mother. Nipple position may also be monitored to ensure that the mother has fully and correctly engaged the breastshield during her pumping session. Feedback of this information to the breast pump could enable optimal application of vacuum to enhance comfort and/or milk output. In another example, the condition of each of the kit components could be analyzed to determine if they need to be repaired or replaced. Other possibilities exist as well. Image or video monitoring of the collection may yield information such as milk ejections; pump duration; flow rate; detection of vacuum settings or changes through the behavior of the nipple, breast or kit; nipple positioning, nipple extension, etc. by application of codification elements and data interpretation in various portions of the breastpump kit (collection system).

Figure 4:
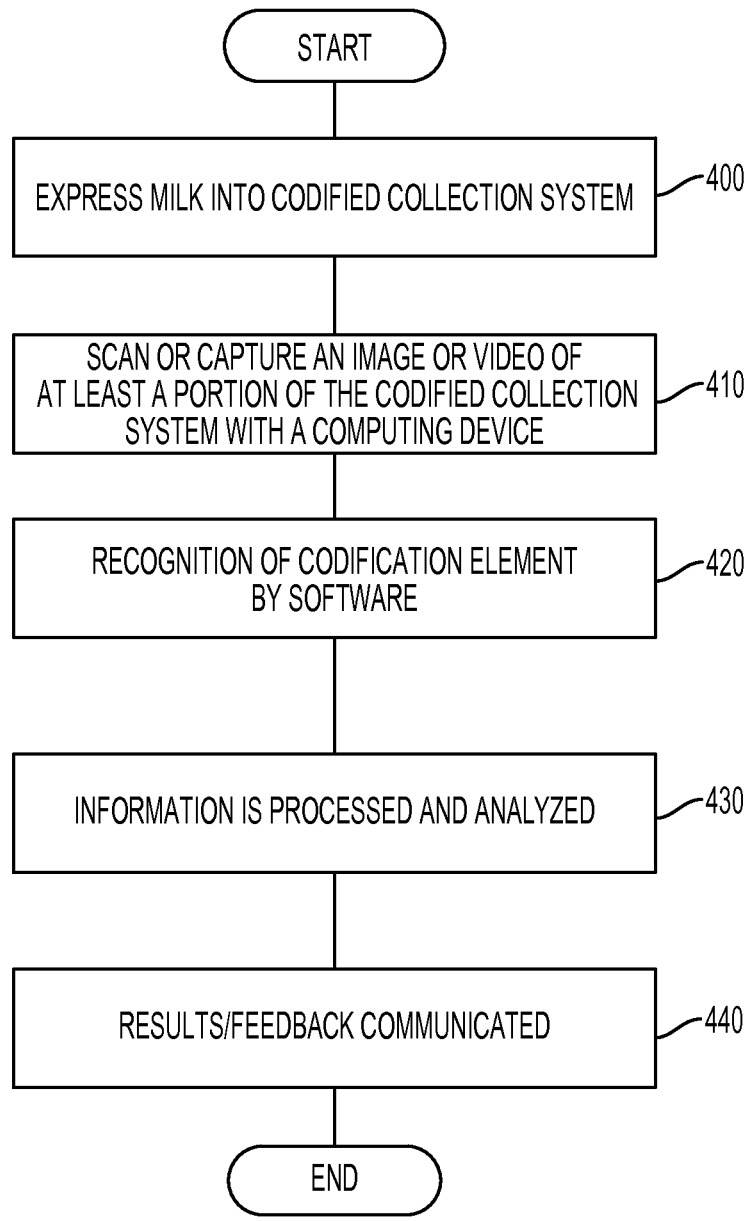
FIG. 4 is a flow chart of an example method of managing a supply of breast milk according to an embodiment.

FIG. 4 is a flow chart of an example method of managing a supply of breast milk according to an embodiment. At step 400, milk is expressed into a codified container. At step 410, an image or video is scanned or captured of the expressed milk in the codified container with a computing device having a camera or other means of capturing an image or video. At step 420, software, such as an app, recognizes the container based on the codification. Based on the recognition, information or feedback regarding the milk, milk supply, performance, etc. is processed and analyzed by the computing device, at step 430. The information may then be displayed or otherwise communicated to the user or other interested party in any suitable manner, at step 440.

Figure 5:
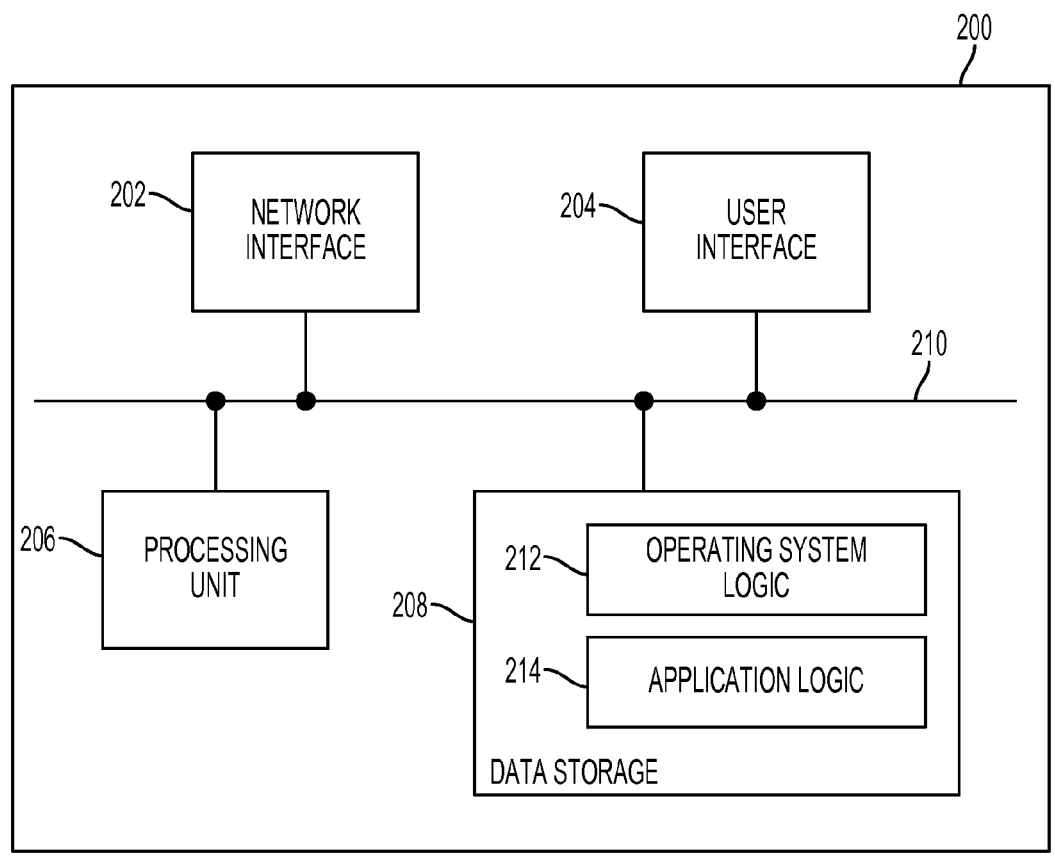
FIG. 5 is a simplified block diagram of an example computing device in which an embodiment may be implemented.

FIG. 5 is a simplified block diagram of an example computing device 200 in which an embodiment may be implemented. The example computing device 200 illustrates the various components such a device may include. The computing device may take any of a variety of forms, examples of which include without limitation a cell phone, a tablet computer, a notebook computer, a desktop computer, a personal digital assistant, a gaming device, or any other type of device now known or later developed. As shown, the representative device 200 includes a network interface 202, a user interface 204, a processing unit 206, and data storage 208, all of which may be communicatively linked together by a system bus, network or other connection mechanism 210.

Network interface 202 may comprise a wired or wireless interface arranged to allow device 200 to communicate on a network (not shown) and with entities via that network, such as with a centralized database (not shown) or a web server (not shown) for instance, and particularly to communicate data to and from the computing device 200. For example, the network interface 202 may comprise a wired or wireless Ethernet interface for communication on a local area network and in turn via a router and/or one or more other network elements with entities on the Internet. As another example, the network interface 202 may comprise a cellular wireless interface, arranged to engage in air interface communication with a radio access network according to a protocol such as LTE, WiMAX, CDMA, GSM, or the like, and via the radio access network with entities on the Internet. Other examples are possible as well.

User interface 204 may enable the device 200 to interact with a user of the device and may thus comprise output components such as a display screen, an audio speaker, and the like, and input components such as a keyboard, camera, touch-pad or touch-screen, and the like. In practice, the user interface may facilitate presentation to the user of the various views discussed above, and may function to receive from a user input of the type discussed above. The software may use the user interface to provide a real time augmented reality view of the image being processed to aid the user in accurate measurement capture.

Processing unit 206 may comprise one or more general purpose processors (e.g., microprocessors) and/or one or more special purpose processors (e.g., application specific integrated circuits, digital signal processors, etc.) If processing unit 206 includes multiple processors, the processors may be arranged to work in combination (e.g., in parallel) or separately. Further, processing unit 206 may be integrated in whole or in part with network interface 202 or with one or more other components of the device.

Data storage 208 may then comprise one or more volatile and/or non-volatile storage components (non-transitory), such as magnetic, optical, flash, or other types of storage now known or later developed, and may be integrated in whole or in part with processing unit 206 and/or may be removable from the device 200 or externally connected (through wired or wireless means) with the device 200. As shown, data storage 208 contains operating system logic 212 and application logic 214 executable by the processing unit 206 to carry out various functions described herein.

Operating system logic 212 may manage hardware resources of the device 200 and provide common services, such as an application programming interface (API), for applications. Examples of such operating systems include, without limitation, ANDROID, iOS, LINUX, MAC OS X, WINDOWS, and WINDOWS PHONE.

Application logic 214, in turn, may include one or more applications, such as the milk supply management application described above, which may be arranged to run on the operating system 212 and thus interact with hardware of the device through operating system 212. These applications may be written in any of a variety of programming languages and compiled into instructions executable by processing unit 206. For instance, the applications may be Java or Objective-C applications, or for that matter other types of applications that, when compiled, will interwork with the API of the operating system 212. Alternatively or additionally, the applications may be defined by one or more markup documents, which can essentially be executed by being interpreted, rendered, or otherwise processed by processing unit 206, possibly through execution of one or more interpreters, such as browser applications.

The advantage of the system described above is evident through the ease and speed with which a mother can collect, track, and ascertain her milk supply and expression performance by merely capturing an image or video of her output. As an example, an application for a computing device, such as a smart phone, can pull all relevant data from the image and her milk pumping session including a date and time stamp, geographic location, container used, milk amount, milk supply and breast expressed to develop her pumping log, performance charts, reminders, etc.

In another embodiment, the imaging and software capabilities contained within the computing device could reside within a breastpump, such as the programmable breastpump described in U.S. Pat. No. 6,547,756, which is hereby incorporated by reference in its entirety.

Thus, while the invention has been described herein with relation to certain embodiments and applications, those with skill in this art will recognize changes, modifications, alterations and the like which still come within the spirit of the inventive concept, and such are intended to be included within the scope of the application.

The invention claimed is:

1. A method for managing a supply of breast milk of a mother, the method comprising:
receiving, via a computing device, at least one image of a container for receiving expressed breast milk, the container including a codification element associated therewith and the at least one image incorporating the codification element;
recognizing the codification element within the at least one image using the computing device;
analyzing the at least one image and codification element using the computing device; and
producing feedback regarding the supply of expressed breast milk based on the analysis.

2. The method of claim 1 wherein the at least one image comprises a series of images.

3. The method of claim 1 wherein analyzing the codification element of the at least one image comprises scaling and orienting the container to calculate an accurate volume.

4. The method of claim 1 wherein the feedback includes at least one of: information regarding the volume of the breast milk within the container, information regarding quality of the breast milk, a pumping log, performance charts, and a reminder.

5. The method of claim 1 wherein the codification element comprises a computer-readable image located on the container.

6. The method of claim 1 wherein the codification element comprises a feature of the container.

7. The method of claim 1 wherein the feedback is provided in real-time.

8. The method of claim 1 further comprising providing the feedback to a user of the computing device.

9. The method of claim 1 further comprising providing the feedback to a healthcare professional.

10. The method of claim 1 further comprising providing the feedback to a breastpump.

11. The method of claim 1 wherein the computing device is in communication with a breastpump.

12. A non-transitory computer readable medium having stored thereon instructions executable by a computing device to cause the computing device to perform functions comprising:
recognizing a codification element contained in an image associated with a container of expressed breast milk;
obtaining information regarding the codification element;
analyzing the image and the codification element; and
providing information regarding the supply of expressed breast milk based on the analysis.

13. The non-transitory computer readable medium of claim 12 wherein analyzing the image and the codification element comprises scaling and orienting the container to calculate an accurate volume.

14. The non-transitory computer readable medium of claim 12 wherein the functions further include automatically correcting for volumetric expansion of frozen breast milk.

15. The non-transitory computer readable medium of claim 12 wherein the codification element comprises a computer readable image located on the container.

16. The non-transitory computer readable medium of claim 12 wherein the codification element comprises information representing a characteristic a feature of the container.

17. The non-transitory computer readable medium of claim 12 wherein the codification element is located within an image of the expressed breast milk, but not on the container.

18. The non-transitory computer readable medium of claim 12 wherein the information includes at least one of: volume of the breast milk within the container, information regarding quality of the breast milk, a pumping log, performance charts, and a reminder.

19. The non-transitory computer readable medium of claim 12 wherein the information is provided in real-time.

20. The non-transitory computer readable medium of claim 12 wherein the information is communicated to a breastpump.

21. The non-transitory computer readable medium of claim 12 wherein the computing device is in communication with a breastpump.

22. A container for collecting expressed breast milk from a mother, the container comprising:
at least one codification element, wherein the at least one codification element is configured to be incorporated into and transmitted in an image, the image configured for receipt and analysis by a computing device to provide analysis and feedback regarding the mother's breast milk supply expressed breast milk within the container based on the image and the codification element information contained therein.

23. The container of claim 22 wherein the computing device is in communication with a breastpump.

24. The container of claim 22 wherein the computing device is connected to a breastpump.

25. The container of claim 22 further comprising a plurality of codification elements.

26. The container of claim 22 wherein the codification element is a computer-readable image.

27. The container of claim 22 wherein the feedback is provided to a user of the computing device.

28. The container of claim 22 wherein the feedback is provided to a healthcare professional.

29. A method for managing the fit of a mother's nipple within a breastshield, the method comprising:
receiving, via a computing device, at least one image of a breastpump kit or portion thereof for receiving expressed breast milk, the breastpump kit including a codification element associated therewith;
recognizing the codification element within the at least one image using the computing device;
analyzing the codification element within the at least one image using the computing device; and
producing feedback regarding the fit of the mother's nipple based on the analysis.

30. The method of claim 29 wherein the codification element is part of the breastshield.

31. The method of claim 29 wherein the feedback includes information regarding nipple positioning.

32. The method of claim 29 wherein the feedback includes information regarding nipple extension.

33. The method of claim 29 wherein the feedback is provided to a breastpump for vacuum application control, comfort, or milk output.

34. The method of claim 29 wherein the codification element is a computer-readable image.

35. The method of claim 29 wherein the feedback is provided in real-time.

36. The method of claim 29 wherein the computing device is in communication with a breastpump.

37. A non-transitory computer readable medium having stored thereon instructions executable by a computing device to cause the computing device to perform functions comprising:
recognizing a codification element within an image associated with a breastpumping kit;
obtaining information regarding the codification element;
analyzing the codification element and the image in combination; and
providing information regarding the fit of the mother's nipple within a breastshield based on the analysis.

38. The non-transitory computer readable medium of claim 37 wherein the codification element is located on a component of the breastpumping kit.

39. The non-transitory computer readable medium of claim 37 wherein the information is provided in real-time.

40. The non-transitory computer readable medium of claim 37 wherein the codification element comprises a computer readable image.

41. The non-transitory computer readable medium of claim 37 wherein the information is communicated to a breastpump.

42. The non-transitory computer readable medium of claim 37 wherein the computing device is in communication with a breastpump.

43. A collection system for collecting expressed breast milk from a mother, the collection system comprising:
a breastpumping kit including a breast shield, a valve, a connector piece, and a collection container; and
at least one codification element, wherein the at least one codification element is configured to be transmitted in an image and analyzed by a computing device to provide analysis and feedback regarding the fit of the mother's nipple within the breast shield.

44. The collection system of claim 43 wherein the codification element is located on a component of the breastpumping kit.

45. The collection system of claim 43 wherein the feedback is communicated to a breastpump.

46. The collection system of claim 43 wherein the computing device is in communication with a breastpump.

47. The collection system of claim 43 wherein the computing device is connected to a breastpump.

48. The collection system of claim 43 further comprising a plurality of codification elements.

49. The collection system of claim 43 wherein the codification element is a computer-readable image.

50. The collection system of claim 43 wherein the feedback is provided to the mother.

51. The collection system of claim 43 wherein the feedback is provided to a healthcare professional.

* * * * *